United States Patent [19]
Woodson

[11] Patent Number: 6,161,541
[45] Date of Patent: Dec. 19, 2000

[54] HYOID EXPANSION AND SUSPENSION PROCEDURE

[75] Inventor: B. Tucker Woodson, Menomennee, Wis.

[73] Assignee: InfluENT Ltd., Herzliya, Israel

[21] Appl. No.: 09/329,170

[22] Filed: Jun. 9, 1999

Related U.S. Application Data

[60] Provisional application No. 60/088,553, Jun. 9, 1998.

[51] Int. Cl.[7] .................................................. A61F 5/56
[52] U.S. Cl. .............................. 128/848; 606/86; 606/232
[58] Field of Search ..................................... 128/898, 848; 606/87, 151, 167, 232

[56] References Cited

U.S. PATENT DOCUMENTS 5,988,171  11/1999  Sohn et al. .............................. 128/848

*Primary Examiner*—Michael Buiz
*Assistant Examiner*—David O. Reip
*Attorney, Agent, or Firm*—Levisohn, Lerner, Berger & Langsam

[57] ABSTRACT

A method is provided for surgically treating obstructive sleep apnea syndrome. In a first embodiment of the invention, a procedure is provided which includes the step of splitting the hyoid bone to open the pharyngeal space anteriorly, posteriorly and laterally, using the mandible as support for both anterior and lateral advancement and expansion, thereby relieving the effects of OSAS. In another embodiment of the invention, a modified version of the first embodiment is provided in which the hyoid is suspended but not split. In this embodiment, the pharyngeal space is increased anteriorly and posteriorly, but to a lesser degree laterally. Splitting the hyoid and distracting it is believed effective as it provides increased pharyngeal space.

5 Claims, 3 Drawing Sheets

HYOID EXPANSION AND SUSPENSION PROCEDURE

RELATED APPLICATIONS

The present application claims the priority benefits of U.S. Provisional Patent Application Ser. No. 60/088,553 filed Jun. 9, 1998. The disclosure of that prior application is incorporated herein by reference.

FIELD OF THE INVENTION

The present invention relates to methods for treatment of obstructive sleep apnea syndrome, upper airway resistance syndrome, sleep disordered breathing and snoring. Background of the Invention Obstructive sleep apnea syndrome (OSAS) is a potentially life threatening disorder, affecting up to 2–4% of the adult population. The syndrome is associated with an absence of airflow, combined with persistent respiratory effort during sleep. It results from a loss of muscular activity of pharyngeal dilators and airway collapse at the hypopharynx—base of the tongue or the oropharynx—soft palate. The hyoid arch and its muscular attachments strongly affect hypopharyngeal airway patency and resistance. Snoring results from vibration of pharyngeal tissues, increased negative inspiratory pressures and airflow limitation in the upper airway.

Upper airway patency during wakefulness and sleep is determined by the interaction between anatomic and physiologic factors. It is common in patients with obstructive sleep apnea syndrome to demonstrate anatomic abnormalities such as mandibular deficiencies, macroglossia, and hypertrophic tonsils. During wakefulness, upper airway patency is maintained by increased muscle activity of the pharyngeal dilators. The onset of sleep results in a reduction of the compensatory dilating muscle activity, thereby increasing the likelihood of upper airway collapse.

Individuals with OSAS and other sleep related breathing disorders frequently have obstruction at the hypopharynx—base or the oropharynx,—and/or soft palate. Movement of the tongue, hyoid, pharynx and larynx are important in maintaining upper airway patency during sleep. The genioglossus muscle, pharyngeal constrictors and hyoepiglothic ligament insert on the hyoid arch (i.e. the hyoglossus, middle constrictor, geniohyoid, mylohyoid, anterior digastric, stemohyoid and thyrohyoid muscles) determine the hypopharyngeal and oropharyngeal airway patency. In unpublished studies, the present inventor has found that advancing the hyoid arch or otherwise changing the anatomic configuration in this area alters retroglossal, retrohyoid, and lateral pharyngeal wall anatomy. Hyolaryngeal techniques which are currently used extensively for hyoid advancement are anatomically limited for anterior advancement of the hyoid. Hyoid expansion using the mandibular arch for support provides greater potential for anterior advancement as well as the opportunity for hyoid expansion.

SUMMARY OF THE INVENTION

It is an object of the invention to provide methods for the treatment of obstructive sleep apnea syndrome (OSAS).

It is a further object of the invention to provide an improved method for treating OSAS in place of the prior art UPPP procedure.

In accordance with the invention, methods are provided for surgically treating obstructive sleep apnea syndrome. In a first embodiment of the invention, a procedure is provided which includes the step of splitting the hyoid bone to open the pharyngeal space anteriorly, posteriorly and laterally, using the mandible as support for both anterior and lateral advancement and expansion, thereby relieving the effects of OSAS. In a second embodiment of the invention, a modified version of the first embodiment is provided in which the hyoid is suspended but not split. In this embodiment, the pharyngeal space is increased anteriorly and posteriorly, but to a lesser degree laterally. Splitting the hyoid and distracting it is unique in that it is believed to be the only method whereby lateral distraction of the pharyngeal space can be achieved.

DETAILED DESCRIPTION OF THE INVENTION AND THE PREFERRED EMBODIMENTS

In accordance with the invention, a method is provided for the surgical treatment of obstructive sleep apnea syndrome. In one of the previous methods taught in the art, known as uvulo-pharyngeal-palatoplasty (UPPP), the lateral portion of the soft palate is removed. The prior art procedure is a painful one, however, with high post-operative morbidity and only partial success. Accordingly, it is an object of the present invention to provide an alternative procedure to the prior art UPPP procedure. However, the invention can also be used with positive results on patients who have previously or concurrently been treated using UPPP, or in conjunction with the UPPP procedure, since combining the procedures may have improved results.

In accordance with the invention, a patient is first placed under general endotracheal anaesthesia. Alternatively, it may be feasible to perform the procedure under local anaesthesia. A shoulder roll is put into place and the patient's head and neck are extended and positioned.

The patient is then prepped and draped in the normal manner. The mandible is outlined with skin marker, indicating the anterior mandibular midline, the outline of the inferior surface of the mandible. Two potential points of insertion for bone screws or anchors are identified and marked on the inferior border of the anterior body of the mandible. Preferred bone screws, anchors, and tools for use in the procedure are described in U.S. patent application Ser. No. 08/883,220, filed Jun. 6, 1997 to Z. Sohn and A. DeRowe, the disclosure of which is fully incorporated herein by reference.

Figure 1A:
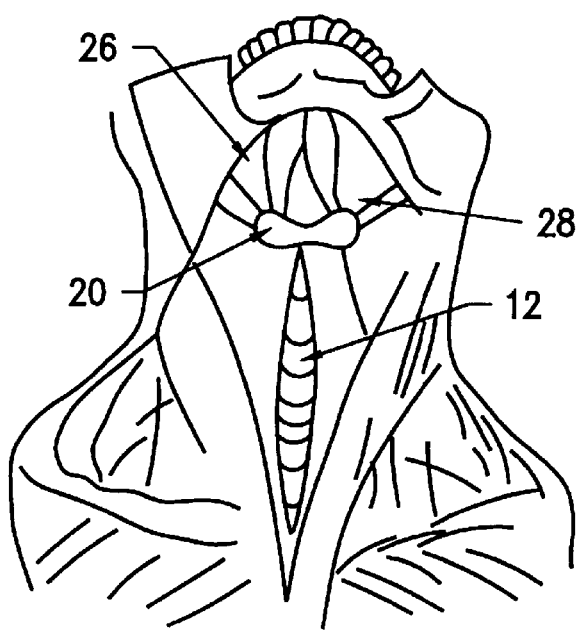
FIG. 1(a) is an anterior view of the anatomy of the neck of an adult.
Figure 1B:
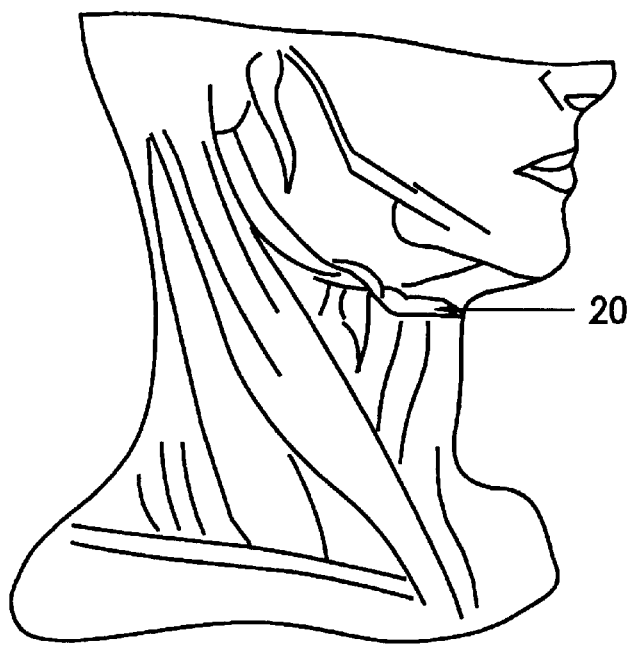
FIG. 1(b) is a lateral view of the muscles of the neck, both prior to performance of the method of the present invention.

As shown in FIG. 1, using the thyroid cartilage 12 as a landmark, the hyoid bone 20 is found, palpated and marked with a skin marker. Anaesthetic, preferably lidocaine with epinephrine 1:100,000, is then injected into the hyoid incision and future stab wound site. A skin incision approximately 3–4 cm in length is made at the superior border of the hyoid, and carried down through the subcutaneous and fatty tissues to the platysma muscle 26. A wheitlander retractor is placed in the wound to improve exposure to the surgical site.

The platysma muscle 26 is split in the midline to expose the hyoid bone 20 further, and dissection is carried down to the suprahyoid musculature of the anterior portion of hyoid 20, with an Allis clamp used to grasp the hyoid. Dissection of the anterior portion of the hyoid 20 is carried out leaving the stylohyoid musculature 28 and ligament intact.

Figure 2A:
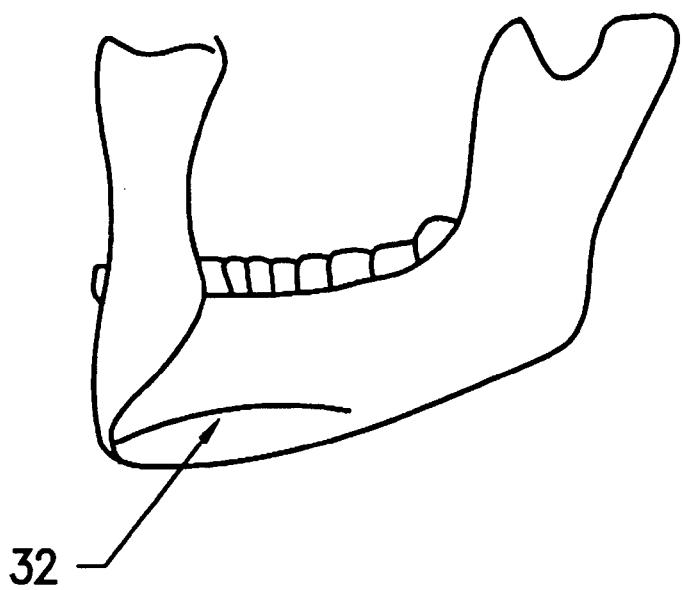
FIG. 2(a) is a left posterior view of the mandible of an adult, prior to performance of the method of the present invention.
Figure 2B:
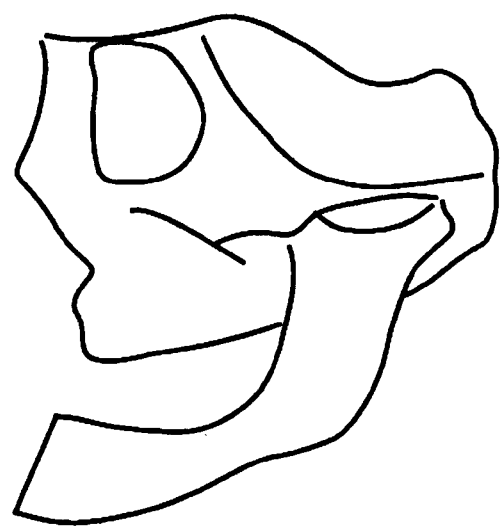
FIG. 2(b) is a left view of a portion of a shell, including the mandible.

Bilateral stab incisions less than 1 cm in length are made approximately 3–4 cm posterior to the anterior midline along the inferior border of the mandibular body about the level of the digastric fossa 32 of the mandible, which is shown in FIG. 2(a). The incisions are preferably widened with hemostats to accommodate a bone screw inserter, preferably the REPOSE™ bone screw inserter, disclosed in the common assignee's copending application Ser. No. 08/733,798, filed Oct. 18, 1996, and manufactured by Influence, Inc. of San Francisco, Calif. The inserter is placed into the right sided stab incision and the screw positioned on the inferior medial surface of the mandible, about the level of the digastric fossa 32, positioned at 90 degrees to the insertion point of the screw. With the safety removed, and the operate button pressed, the screw is inserted into the mandible such that the screw is fully within the mandible, and having no protrusion therefrom. Screw insertion is then repeated on the contralateral side. Both sites are palpated to ensure that the screws are flush with the mandible's surface.

At this stage, the sutures from the bone screws are now protruding from the stab incisions. The still looped end of the polypropylene suture is loaded into a suture passer, preferably one of those disclosed in the prior patent application cited above. The suture passer is introduced into the right-sided stab wound and passed inferiorly under the subcutaneous tissues to exit at a point just above the hyoid bone 20. The procedure is then repeated on the contralateral side, following which the sutures are released from the passer.

Figure 3A:
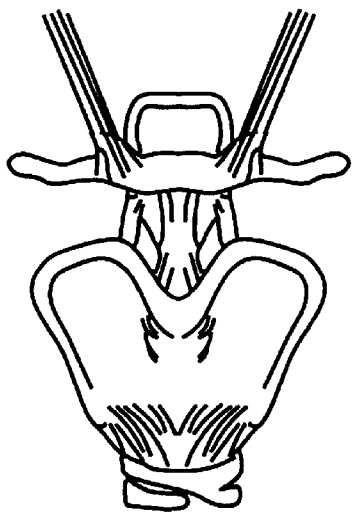
FIG. 3(a) is an anterior view of the hyoid bone of an adult prior to performing the procedure of the present invention.
Figure 3B:
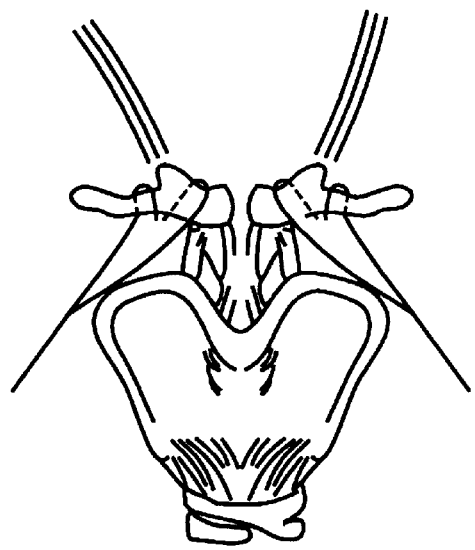
FIG. 3(b) is an anterior view of the same hyoid bone shown in FIG. 3(a), after splitting of the hyoid at its midline, and at the commencement of distraction of the hyoid.
Figure 3D:
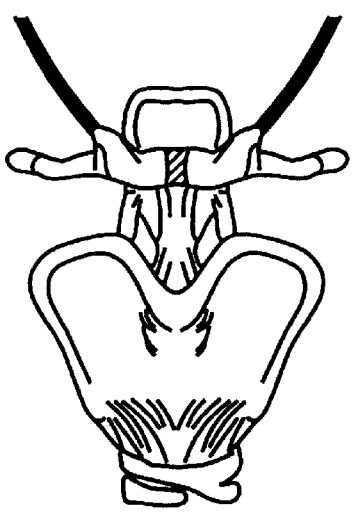
FIG. 3(d) is an anterior view of the hyoid shown in FIGS. 3(a), 3(b) and 3(c), showing the hyoid after completion of both the distraction step, and the tying of the hyoid using suture thread.
Figure 3C:
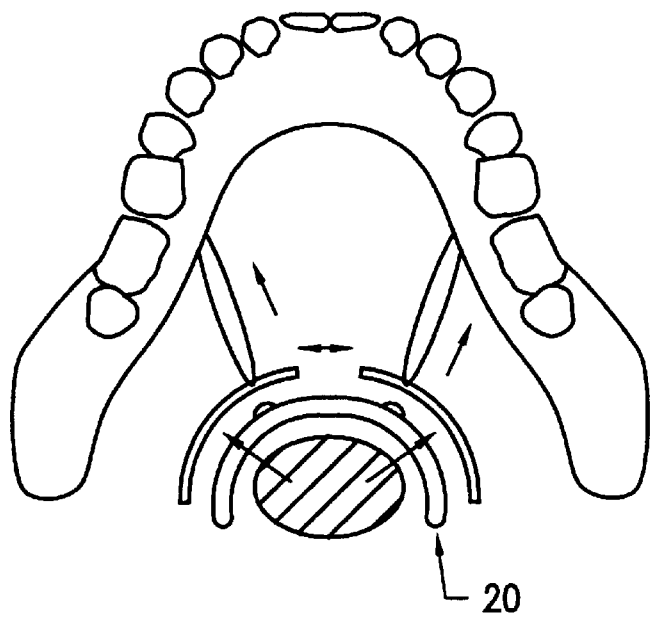
FIG. 3(c) is a top plan view of the airway after the hyoid is split at its midline and pulled toward the mandible.

As shown in FIGS. 3(a)–(d), in accordance with a first embodiment of the invention, a sagittal saw is then used to split the hyoid bone 20. FIG. 3(a) illustrates the intact hyoid 20, prior to splitting with the sagittal saw. Using the sagittal saw, hyoid 20 is split at the hyoid's midline into right and left halves as shown in FIG. 3(b). A small miniplate, crimper or other fixation is used to separate the divided ends of the body of the hyoid bone.

After sawing the bone, the right-sided loop of polypropylene suture is cut to make two separate strands of suture. One strand is loaded onto an appropriately sized Mayo needle. This suture is passed around the right portion of the split hyoid, from the superior portion of the hyoid to emerge at the hyoid's inferior portion. This is then repeated again on the right side, creating a two-strand wraparound of the suture from the hyoid's superior to inferior portion. After completion of the two-strand wraparound on the right side, this procedure is repeated for the left side of the split hyoid, with the second set of sutures.

The right-sided suture strands are tied loosely at first, to see the extent of the distraction of the muscles and pharynx. Once it is determined that enough tension has been provided, the knot is secured. If tension is insufficient, the wraparound of the suture is adjusted accordingly. Examination of distraction and of suture tension, with adjustment if needed, is then repeated on the contralateral side.

When the sutures have been tied on both sides with sufficient tension, a small penrose drain is placed just above the hyoid 20. The platysma 26 and subcutaneous tissues are approximated with interrupted 3-0 Chromic. The skin is closed with interrupted sutures, although, alternatively, a subcuticular plastic closure can be performed as well. Both stab wounds are closed in the same manner. The dressings preferably consist of Xeroform gauze, 4×4's folded and opened lengthwise and secured with plastic tape. A second embodiment of the procedure is division of the hyoid bone without placement of a miniplate, crimper or other means of fixation or separation.

In accordance with the invention, the hyoid distraction expansion procedure described above opens the pharyngeal space anteriorly, posteriorly and laterally. Alternatively, in a third embodiment of the invention, a hyoid suspension can be performed. In accordance with the second embodiment, the hyoid suspension is performed in the same manner described above, but without the splitting of the hyoid. In this second embodiment, the pharyngeal space is only increased anteriorly and posteriorly. In the case of a combined-UPPP procedure, UPPP (i.e. a reshaping of the soft palate to open the posterior airway) is performed.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

I claim as follows:

1. A method for surgically treating sleep related breathing disorders, comprising the steps of:
   inserting a holding means into a mandible;
   splitting a hyoid bone at a midline into a right half, a left half and an opening therebetween;
   expanding said opening by pulling apart said left half from said right half, thereby increasing the pharyngeal space anteriorly, posteriorly and laterally;
   securing said opening by attaching said right half and said left half of said hyoid bone to said holding means in the mandible; and
   adjusting the secured halves of said hyoid bone to ensure adequate muscle tension.

2. A method for surgically treating sleep related breathing disorders according to claim 1, further comprising the step of putting a spacer means in said opening.

3. A method for surgically treating sleep related breathing disorders according to claim 2, wherein said spacer means is a plate.

4. A method for surgically treating sleep related breathing disorders according to claim 2, wherein said spacer means is a crimper.

5. A method for surgically treating sleep related breathing disorders according to claim 1, wherein said holding means comprises at least one bone screw.

* * * * *